(12) United States Patent
Ranjan et al.

(10) Patent No.: US 10,335,376 B2
(45) Date of Patent: *Jul. 2, 2019

(54) RALOXIFENE SPRINKLE COMPOSITION

(71) Applicant: Sun Pharmaceutical Industries Limited, Mumbai, Maharashtra (IN)

(72) Inventors: Ujjwal Ranjan, Bokaro (IN); Mona Dhaliwal, Saharanpur (IN); Mukesh Kumar Garg, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/050,199

(22) Filed: Jul. 31, 2018

(65) Prior Publication Data

US 2018/0333364 A1   Nov. 22, 2018

Related U.S. Application Data

(63) Continuation of application No. 15/839,221, filed on Dec. 12, 2017, now Pat. No. 10,092,522, which is a continuation of application No. 15/608,387, filed on May 30, 2017, now Pat. No. 9,872,838.

(30) Foreign Application Priority Data

May 30, 2016   (IN) .............................. 201611018447

(51) Int. Cl.
    *A61K 9/48*      (2006.01)
    *A61K 31/4535*   (2006.01)
    *A61K 9/50*      (2006.01)
    *A61K 31/38*     (2006.01)

(52) U.S. Cl.
    CPC .......... *A61K 9/4866* (2013.01); *A61K 9/4808* (2013.01); *A61K 9/4858* (2013.01); *A61K 9/5026* (2013.01); *A61K 9/5031* (2013.01); *A61K 9/5036* (2013.01); *A61K 9/5042* (2013.01); *A61K 9/5047* (2013.01); *A61K 9/5078* (2013.01); *A61K 31/38* (2013.01); *A61K 31/4535* (2013.01); *H05K 999/99* (2013.01)

(58) Field of Classification Search
    CPC ..................................................... A61K 9/5078
    See application file for complete search history.

(56) References Cited

U.S. PATENT DOCUMENTS

| | | | |
|---|---|---|---|
| 6,458,811 B1 | 10/2002 | Arbuthnot et al. | |
| 6,707,719 B2 | 3/2004 | Shibata et al. | |
| 6,894,064 B2 | 5/2005 | Arbuthnot et al. | |
| 8,030,330 B2 | 10/2011 | Arbuthnot et al. | |
| 8,840,924 B2 * | 9/2014 | Tengler | A61K 9/0056 424/466 |
| 9,872,838 B2 * | 1/2018 | Ranjan | A61K 9/4866 |
| 2004/0185170 A1 | 9/2004 | Chungi et al. | |
| 2010/0145057 A1 | 6/2010 | Thennati et al. | |
| 2013/0202713 A1 | 8/2013 | Bele et al. | |

FOREIGN PATENT DOCUMENTS

| EP | 0910369 A1 | 4/1999 |
|---|---|---|
| WO | WO-2004/052345 A1 | 6/2004 |
| WO | WO-2008/157228 A1 | 12/2008 |
| WO | WO-2012/156997 A2 | 11/2012 |

OTHER PUBLICATIONS

Extended European Search Report for EP application No. 17173535.0-1468, dated Sep. 9, 2017.

* cited by examiner

*Primary Examiner* — Carlos A Azpuru
(74) *Attorney, Agent, or Firm* — Goodwin Procter LLP

(57) ABSTRACT

The present invention relates to a capsule composition of raloxifene comprising multiparticulates comprising a) a core comprising raloxifene, and b) a taste-masking coating present in amount of from about 0.5% to about 50% w/w based on the core weight.

4 Claims, No Drawings

RALOXIFENE SPRINKLE COMPOSITION

RELATED APPLICATIONS

This is a continuation application of U.S. application Ser. No. 15/839,221, filed Dec. 12, 2017, which is a continuation application of U.S. application Ser. No. 15/608,387, filed May 30, 2017 which claims priority to Indian Application IN201611018447, filed May 30, 2016, each of which is hereby incorporated by reference in its entirety.

FIELD OF THE INVENTION

The present invention relates to a capsule composition comprising plurality of particulates comprising a) a core comprising raloxifene, and b) a taste-masking coating present in an amount of from about 0.5% to about 50% w/w based on the core weight.

BACKGROUND OF THE INVENTION

Raloxifene is indicated for the treatment of osteoporosis and breast cancer in postmenopausal women. It is commercially available as immediate release tablets (Evista®) in the U.S. The development of raloxifene composition has been hindered, due to low water solubility which can adversely affect the bioavailability and manufacturing process. U.S. Pat. No. 6,458,811 discloses raloxifene having a mean particle size of less than 25 microns, which allows enhanced bioavailability and control during the manufacturing process. It further discloses granular compositions comprising raloxifene, which can be compressed into tablet dosage forms or can be filled into capsules.

Raloxifene is known to possess a bitter taste. Raloxifene is categorized as a drug that should be "handled as hazardous" by the National Institute for Occupational Safety and Health (U.S.). Further, the summary of product characteristic by the European Medicines Agency instructs to "not break or crush" Evista® tablets, as they may taste bad. Handling of uncoated granules and crushed tablets would also be hazardous for the compounding pharmacist.

Thus, there exists a need in the art to formulate a composition of raloxifene which provides for better patient compliance for patients that have difficulty in swallowing. However, masking the bitter taste as well as achieving the desired immediate release profile would be challenging for a drug with poor aqueous solubility.

Hence, the present inventors have now developed plurality of particulates of raloxifene, which can be administered by sprinkling multiparticulates on soft food and have a desired in-vitro release. The present invention would provide advantages for patients who have difficulty in swallowing the conventional solid oral composition. Further, the sprinkle composition of the present invention has high drug-loading, leading to a minimal total weight of the composition, which can be easily handled and taken by the patients.

SUMMARY OF THE INVENTION

The present invention relates to a capsule composition comprising plurality of particulates comprising a) a core comprising raloxifene, and b) a taste-masking coating present in amount of from about 0.5% to about 50% w/w based on the core weight.

The present invention can be administered as an intact capsule as well as a sprinkle composition.

DETAILED DESCRIPTION OF THE INVENTION

A first aspect of the present invention relates to a capsule composition of raloxifene comprising plurality of particulates s, wherein said capsules release not more than 40% of raloxifene in 10 minutes, when measured in a United States Pharmacopeia (USP) type 2 dissolution apparatus, paddle at 50 RPM, at a temperature of 37° C.±0.5° C. in 1000 mL of pH 4.5 acetate buffer and 0.05% sodium lauryl sulfate.

A second aspect of the present invention relates to a capsule composition of raloxifene comprising plurality of particulates, wherein said capsules release not more than 85% of raloxifene in 10 minutes, when measured in a USP type 2 dissolution apparatus, paddle at 100 RPM, at a temperature of 37° C.±0.5° C. in 1000 mL of water, 0.5% polysorbate, and an enzyme.

According to one embodiment of this aspect, the raloxifene may be present in an amount of from about 10% to about 80% based on the total weight of composition. In particular, from about 15% to about 80% based on the total weight of composition, wherein the capsule shell weight is not included in the total weight of composition.

A third aspect of the present invention relates to a capsule composition of raloxifene comprising multiparticulates having raloxifene in an amount of from about 10% to about 80%, e.g. about 20% to about 60%, or about 30 to about 40%, based on the total fill weight of the capsule, where said capsule is bioequivalent to the marketed raloxifene tablets.

According to one embodiment of this aspect, the total fill weight is less than about 600 mg. In particular, the total fill weight is between about 75 mg and about 600 mg, wherein the capsule shell weight is not included into the total fill weight of the capsule.

According to another embodiment of this aspect, the capsule size is 0 or less. In particular, the capsule size is 1 or less.

Bioequivalence is established by comparing pharmacokinetic parameters, for example AUC and $C_{max}$, of the intact capsule composition of the present invention with Evista® tablets in healthy human subjects.

The term "AUC" refers to the area under the time/plasma concentration curve following administration of a raloxifene pharmaceutical composition.

The term "$C_{max}$" refers to the maximum concentration of raloxifene in the blood following the administration of a raloxifene pharmaceutical composition.

According to another embodiment of this aspect, the capsules, when administered to healthy subjects under fasting conditions, provide a mean $C_{max}$ value in the range of from about 2.5 ng/mL/mg to about 15 ng/mL/mg.

According to one embodiment of the above aspects, the multiparticulates have a bulk density of from about 0.30 g/mL to about 0.80 g/mL.

According to another embodiment of the above aspects, the multiparticulates may be in the form of a core and coating.

According to another embodiment of the above aspects, the coating is present in an amount of from about 0.5% to about 40% w/w based on the core weight.

According to another embodiment of the above aspects, the raloxifene has a $D_{90}$ particle size of not more than 35 μm.

According to another embodiment of the above aspects, the coated cores have a $D_{90}$ particle size of less than or equal to 900 µm, e.g., equal to about 800 µm, for example, about 200 to about 500 microns, e.g., about 800 µm, or e.g., having about 60 to about 40 ASTM sieve size.

The term "$D_{90}$ value" as used in this application, means that 90% of the extended release coated cores have a volume diameter in the specified range when measured by a light scattering method such as a Malvern® Mastersizer®.

According to another embodiment of the above aspects, the coating is a taste-masking coating.

According to another embodiment of the above aspects, the taste-masking coating comprises a taste-masking polymer.

According to another embodiment of the above aspects, the taste-masking coating further comprises a sweetener.

According to another embodiment of the above aspects, the particulates are further blended with a lubricant.

According to another embodiment of the above aspects, the lubricant is present in an amount of from about 0.1% to about 15% by total weight of the composition.

According to another embodiment of the above aspects, the particulates are further blended with disintegrants.

According to another embodiment of the above aspects, the capsule composition is stable when subjected to stability conditions at a temperature of 40° C. and relative humidity ("RH") of 75% for a period 6 months.

According to another embodiment of the above aspects, the stable sprinkle capsule composition, when sprinkled on soft food, is not impacted by soft foods of different pH levels.

According to another embodiment of the above aspects, the stable sprinkle capsule composition, produce relative substance not more than 1% w/w when sprinkled on soft food for at least 30 minutes.

The term "stable" as used herein means that the capsule composition, when subjected to stability conditions at a temperature of 40° C. and RH of 75% for a period 6 months, produces the raloxifene-related compound C not more than 1%. Further, the particulates are stable for at least 60 minutes after being sprinkled onto soft foods of different pH levels.

According to another embodiment of the above aspects, the raloxifene is not present in intimate contact with an alkaline excipient.

"Intimate contact" as used herein means that alkaline excipients are present in the core or the coating dispersion together with raloxifene.

Alkaline excipients used herein may include but are not limited to calcium phosphate, magnesium phosphate, aluminum phosphate, magnesium carbonate, croscarmellose, and mixtures thereof.

The term "raloxifene" refers to raloxifene base, as well as other pharmaceutically acceptable salts, in particular hydrochloride. Raloxifene may be present in the sprinkle composition in an amount of from about 20 mg to about 100 mg. Raloxifene may be present in an amount of from about 15% to about 80% based on the total weight of composition.

The term "sprinkle composition" as used herein refers to a composition which can be sprinkled onto soft foods such as apple sauce, yogurt, cottage cheese, and pudding, or into drinks, and then administered orally to patients. The composition may also be administered through an NG-tube or a G-tube in patients who cannot swallow.

The term particulates" as used herein includes pellets, beads, granules, spheres, and mini-tablets. These particulates may be in the form of coated cores. The coated cores may have single or multiple coatings. The coated cores may be prepared by coating raloxifene, optionally along with other pharmaceutically acceptable excipients, onto an inert bead. Optionally, a seal coat layer may be present between the inert beads and said coating layer comprising raloxifene. The coated cores may be further coated, preferably by a taste-masking coating. The inert beads may be water-soluble, water-swellable, or water-insoluble. Examples of water-swellable cores include microcrystalline cellulose spheres such as Celphere®. Examples of water-soluble cores include sugar spheres made of glucose, mannitol, lactose, xylitol, dextrose, sucrose, and combinations thereof. Examples of water-insoluble cores include glass beads and silicon dioxide beads. The inert cores have a $D_{90}$ particle size of less than or equal to about 800 µm.

According to another embodiment of the above aspects, the coated cores are prepared by coating with a raloxifene dispersion in an amount of from about 80% to about 150% by total weight of the inert cores.

According to another embodiment of the above aspects, the raloxifene dispersion comprises a surfactant.

Alternatively, the particulates may be in the form of matrix cores, formulated by mixing raloxifene, optionally with other pharmaceutically acceptable excipients, followed by granulation, direct compression, or extrusion-spheronization. Optionally, the matrix cores may be coated.

A fourth aspect of the present invention relates to a capsule composition comprising a plurality of particulates comprising
a) a core comprising raloxifene; and
b) a taste-masking coating over the core
wherein the taste-masking coating is present in an amount of from about 0.5% to about 50%, or about 0.5% to about 40% w/w, e.g., about 10% to about 30% or 40% w/w based on the core weight.

The taste masking coating may comprise one or more taste-masking polymers and coating additives. Pharmaceutically acceptable coating additives may be sweeteners, pore-formers, plasticizers, anti-tacking agents, opacifiers, coloring agents, disintegrants, coating agents, and mixtures thereof.

Suitable taste-masking polymers are selected from the group comprising water soluble/water swellable polymers such as hydroxy ethyl cellulose, hydroxy propyl cellulose, and hypromellose; water insoluble polymers such as ethyl cellulose, polycarbophil, and polyacrylic acid; and mixtures thereof. Taste-masking polymers may also be enteric, such as cellulose acetate butyrate, cellulose acetate phthalate, ethyl vinyl phthalate, polyvinyl acetate phthalate, hydroxy alkyl cellulose phthalates, methacrylic acid/ethyl acrylate copolymers, and mixtures thereof. In particular, the taste-masking polymer is a water-insoluble polymer, for example ethyl cellulose. In particular, the taste-masking polymer is a water-soluble polymer, alone or in combination with a water-insoluble polymer. These may be present in the composition in the range of from about 0.01% w/w to about 25% w/w of the composition.

Examples of pore-formers include calcium carbonate, calcium phosphate, calcium saccharide, calcium succinate, calcium tartrate, ferric acetate, ferric hydroxide, ferric phosphate, magnesium carbonate, magnesium citrate, magnesium hydroxide, magnesium phosphate, hypromellose such as HPMC E5, and mixtures thereof. These may be present in the composition in the range of from about 0.01% w/w to about 15% w/w of the composition.

Examples of sweeteners include, but are not limited to, sucrose, sucralose, sorbitol, xylitol, dextrose, fructose, maltitol, acesulfame potassium, aspartame, saccharin, saccharin sodium, maltitol, glucose, cyclamate, sodium cyclamate, and mixtures thereof. These may be present in the composition in the range of from about 0.1% w/w to about 20% w/w of the total weight of the composition.

Examples of plasticizers include propylene glycol, triethyl citrate, tributyl citrate, dibutyl sebacate, acetyl tributyl citrate, glyceryl monostearate, triacetin, polyethylene glycol, diethyl phthalate, acetylated monoglycerides, diacetylated monoglycerides, cetyl alcohol, and mixtures thereof.

Examples of anti-tacking agent include talc, glyceryl monostearate, vegetable oil, waxes, a blend of magnesium stearate and sodium lauryl sulfate, boric acid, sodium benzoate, sodium acetate, sodium chloride, polyethylene glycol, sodium oleate, sodium lauryl sulfate, magnesium lauryl sulfate, corn starch, amorphous silicon dioxide, Vitamin E, Vitamin E TPGS, and mixtures thereof.

Examples of opacifiers include titanium dioxide, manganese dioxide, iron oxide, silicon dioxide, and mixtures thereof. These may be present in the composition in the range of from about 0.01% w/w to about 15% w/w of the composition, e.g., about 1% w/w to about 4% w/w.

Suitable solvents are selected from the group comprising purified water, ethyl alcohol, isopropyl alcohol, acetone, and mixtures thereof.

Coating may be carried out by using any conventional coating techniques known in the art, such as spray coating using a fluidized bed processor or pan coating.

The pharmaceutical composition may further comprise other pharmaceutically acceptable excipients. Examples of pharmaceutically acceptable excipients include binders, diluents, lubricants/glidants, disintegrants, surfactants, and mixtures thereof.

Examples of fillers or diluents include, but are not limited to, lactose, sorbitol, calcium dihydrogen phosphate dihydrate, calcium phosphate-dibasic, calcium phosphate-tribasic, calcium sulfate, microcrystalline cellulose, silicified microcrystalline cellulose, mannitol, starch, pregelatinized starch, and mixtures thereof.

Examples of binders include, but are not limited to, corn starch, pregelatinized starch, microcrystalline cellulose, silicified microcrystalline cellulose, methyl cellulose, hydroxypropyl cellulose (HPC-L), methylcellulose, carboxymethyl cellulose sodium, hydroxypropyl methylcellulose, polyvinylpyrrolidone, and mixtures thereof.

Examples of disintegrants include, but are not limited to, cross-linked polyvinyl pyrrolidone, corn starch, modified starches, agar-agar, calcium carbonate, sodium carbonate, alginic acids, croscarmellose sodium, sodium starch glycolate, microcrystalline cellulose, hydroxypropyl cellulose (L-HPC), and mixtures thereof. These may be present intragranularly or extragranularly. The disintegrant may be added at the lubrication stage.

Examples of lubricants and glidants include, but are not limited to, colloidal anhydrous silica, croscarmellose sodium, stearic acid, magnesium stearate, glyceryl behenate, calcium stearate, sodium stearyl fumarate, talc, microcrystalline wax, yellow beeswax, white beeswax, and mixtures thereof.

Examples of surfactants include, but are not limited to, sorbitan monostearate, polyoxythylene sorbitan monostearate such as polysorbate 60 or polysorbate 80, non-ethoxylated glyceryl monostearate, cetomacrogol, cetostearyl alcohol, sodium stearoyl lactylate, lecithin, sodium lauryl sulfate and mixtures thereof.

The coloring agents and flavoring agents of the present invention may be selected from any FDA-approved colors or flavors for oral use.

The disclosure also provides for a plurality of particulates, for example, contained within a capsule, wherein each particulate comprises an inert core; a drug layer disposed on the inert core, where the drug layer comprises raloxifene hydrochloride and a polymer such as povidone; a taste masking layer over the drug layer, comprising a polymer such as hypromellose and optionally a sweetener (e.g., sucralose), and optionally a lubricant layer over the taste masking layer, comprising e.g., at least one of sodium stearyl fumarate, silicon dioxide, and croscarmellose sodium (e.g., equal parts by weight).

The term "about," as used herein, refers to any value which lies within the range defined by a variation of up to ±10% of the value.

The following examples represent various embodiments according to the present invention. The examples are given solely for the purpose of illustration and are not to be construed as limitations of the present invention, as many variations thereof are possible without departing from the spirit and scope of the invention.

Example 1

| Ingredients | Quantity (mg) |
|---|---|
| Drug layered cores | |
| Raloxifene hydrochloride | 60.00 |
| Sugar spheres | 60.00 |
| Polysorbate 80 | 4.00 |
| Povidone | 9.00 |
| Sucralose | 2.00 |
| Purified water | q.s. |
| Taste-masking coating | |
| Ethyl cellulose | 3.88 |
| Hypromellose | 15.47 |
| Talc | 4.17 |
| Magnesium stearate | 2.00 |
| Sucralose | 0.50 |
| Isopropyl alcohol | q.s. |
| Purified water | q.s. |
| Lubrication | |
| Sodium stearyl fumarate | 1.62 |
| Colloidal silicon dioxide | 1.62 |
| Croscarmellose sodium | 1.62 |

Manufacturing Process:
1. Raloxifene, povidone, polysorbate 80, and sucralose were dispersed in purified water to obtain a drug dispersion.
2. Sugar spheres were coated with the drug dispersion of step 1 to obtain drug layered cores.
3. Hypromellose, ethyl cellulose, magnesium stearate, sucralose, and talc were dispersed in a mixture of isopropyl alcohol and purified water to obtain a dispersion.
4. The drug coated cores of step 2 were coated with the dispersion of step 3 to obtain taste-masked coated cores.
5. Sodium stearyl fumarate, croscarmellose sodium, and colloidal silicon dioxide were mixed with the taste-masked coated cores of step 4 to obtain lubricated coated cores.

Example 2

The lubricated coated cores of Example 1 were filled into size 2 capsules.

Example 3

| Ingredients | Quantity (mg/capsule) |
|---|---|
| Drug layered cores | |
| Raloxifene hydrochloride | 60.00 |
| Sugar spheres | 60.00 |
| Polysorbate 80 | 4.00 |
| Povidone | 9.00 |
| Sucralose | 2.00 |
| Purified water | q.s. |

-continued

| Ingredients | Quantity (mg/capsule) |
|---|---|
| Taste-masking coating | |
| Hypromellose | 13.50 |
| Sucralose | 6.00 |
| Talc | 5.50 |
| Magnesium stearate | 2.00 |
| Purified water | q.s. |
| Lubrication | |
| Sodium stearyl fumarate | 1.62 |
| Colloidal silicon dioxide | 1.62 |
| Croscarmellose sodium | 1.62 |

Manufacturing Process:
1. Raloxifene, povidone, polysorbate 80, and sucralose were dispersed in purified water to obtain a drug dispersion.
2. Sugar spheres were coated with the drug dispersion of step 1 to obtain drug layered cores.
3. Hypromellose, magnesium stearate, sucralose, and talc were dispersed in purified water to obtain a dispersion.
4. The drug coated cores of step 2 were coated with the dispersion of step 3 to obtain taste-masked coated cores.
5. Sodium stearyl fumarate, croscarmellose sodium, and colloidal silicon dioxide were mixed with the taste-masked coated cores of step 4.
6. The lubricated coated cores of step 5 were filled into suitable sized capsules, e.g., capsule size 2.

Example 4

| Ingredient | mg/capsule |
|---|---|
| Drug layered cores | |
| Raloxifene hydrochloride USP | 60.000 |
| Sugar spheres (40/60 mesh ASTM) | 60.000 |
| Polysorbate 80 | 4.000 |
| Povidone | 9.000 |
| Sucralose | 2.000 |
| Purified water | q.s. |
| Taste-masking coating | |
| Ethyl cellulose | 3.867 |
| Hypromellose | 15.465 |
| Talc | 4.168 |
| Magnesium stearate | 2.000 |
| Sucralose | 1.500 |
| Isopropyl alcohol | q.s. |
| Purified water | q.s. |
| Lubrication | |
| Sodium stearyl fumarate | 1.620 |
| Colloidal silicon dioxide | 1.620 |
| Croscarmellose sodium | 1.620 |

Manufacturing Process:
1. Raloxifene, povidone, polysorbate 80, and sucralose were dispersed in purified water to obtain a drug dispersion.
2. Sugar spheres were coated with the drug dispersion of step 1 to obtain drug layered cores.
3. Hypromellose, ethyl cellulose, magnesium stearate, sucralose, and talc were dispersed in a mixture of isopropyl alcohol and purified water to obtain a dispersion.
4. The drug coated cores of step 2 were coated with the dispersion of step 3 to obtain taste-masked coated cores.
5. Sodium stearyl fumarate, croscarmellose sodium, and colloidal silicon dioxide were mixed with the taste-masked coated cores of step 4 to obtain lubricated coated cores.
6. The lubricated coated cores of step 5 were filled into size 2 capsules.

Dissolution Study of Example 1 in Dissolution Media I

The dissolution study was performed in 1000 mL of pH 4.5 acetate buffer and 0.05% sodium lauryl sulfate in USP II apparatus at 50 RPM. The samples were analyzed by high performance liquid chromatography (HPLC)/UV.

Dissolution Study of Example 4 in Dissolution Media II

The dissolution study was performed in 1000 mL of water, 0.5% polysorbate, and pepsin (pepsin may be replaced with bromelain) in USP II apparatus at 100 RPM. The samples were analyzed by HPLC/UV.

TABLE 1

Percentage release of Example 1 and Example 4 in dissolution media I and II

| | Time (minutes) | | | |
|---|---|---|---|---|
| Percent drug release | 10 | 20 | 30 | 45 |
| Example 1 Dissolution media I | 23 | 29 | 33 | 37 |
| Example 4 Dissolution media II | 75 | 88 | 94 | 97 |

Table 1 shows that Examples 1 and 4 produced desired in-vitro profiles in dissolution media I and dissolution media II.

Pharmacokinetic Parameters of Example 4 Capsules and Evista® Tablets in Healthy Human Subjects Pharmacokinetic studies were conducted by orally administering Example 4 capsules and Evista® tablets to healthy human subjects under fasting conditions.

A single dose randomized, three treatment, four period, four sequence crossover study in healthy human subjects was carried out under fasting conditions to determine pharmacokinetic parameters.

TABLE 2

Pharmacokinetic parameters for Example 4 capsules and Evista ® tablets

| Pharmacokinetic parameters | Ratio (T/R) |
|---|---|
| $C_{max}$ (ng/mL) | 111.13 |
| $AUC_{0-inf}$ (ng · hr/mL) | 112.66 |

TABLE 3

| Pharmacokinetic parameters | Example 4 |
|---|---|
| Mean $C_{max}$ (ng/mL/mg) | 7.0 |

Table 2 shows that Example 4 capsules were found to be bioequivalent to the marketed raloxifene tablets.

Stability:

In Vitro Soft Food Studies a) Related Substances

A capsule of Example 4 was opened, and the particulates therein were tested for related substances after exposure to applesauce or chocolate pudding for 60 minutes.

The coated discrete units were found to be stable in applesauce and chocolate pudding, with regard to related substances as given in Table 4.

TABLE 4

Related substances of particulates after exposure to applesauce and chocolate pudding

| | Exposure time 0 min (applesauce) | Exposure time 60 min (applesauce) | Exposure time 0 min (chocolate pudding) | Exposure time 60 min (chocolate pudding) |
|---|---|---|---|---|
| Impurity-C (Related Compound C) (% w/w) | 0.06 | 0.06 | 0.02 | 0.03 |
| Total related substances (% w/w) | 0.15 | 0.17 | 0.13 | 0.13 | b) Assay

A capsule of Example 4 was opened, and the multiparticulates therein were tested for assay after exposure to various soft foods for 60 minutes. The multiparticulates were found to be stable with regard to assay, as given in Table 5.

TABLE 5

Assay of coated discrete units after exposure to various soft foods

| Soft food | Exposure time 0 min | Exposure time 60 min |
|---|---|---|
| Applesauce | 101.7% | 101.6% |
| Yogurt | 100.5% | 99.2% |
| Pudding | 98.3% | 97.8% |

Based on the in vitro soft food studies, it was concluded that stability is not impacted by soft foods having different pH levels.

We claim:

1. A sprinkle capsule composition comprising a plurality of particulates, wherein each particulate comprises:
   a) a core comprising raloxifene; and
   b) a taste-masking coating over the core to form coated cores having a $D_{90}$ particle size of less than or equal to 900 μm;
   wherein, the particulates are stable when sprinkled on a soft food and wherein raloxifene is present in an amount from about 10% to about 80% based on the total weight of the composition.

2. The sprinkle capsule composition according to claim 1, wherein the soft food comprises apple sauce, yogurt, cottage cheese, pudding or drinks.

3. A sprinkle capsule composition comprising a plurality of particulates, wherein each particulate comprises:
   a) a core comprising raloxifene; and
   b) a taste-masking coating over the core;
   wherein, the particulates are stable for at least 60 minutes when sprinkled on a soft food and wherein raloxifene is present in an amount from about 10% to about 80% based on the total weight of the composition.

4. The sprinkle capsule composition according to claim 3, wherein the composition produces relative substance not more than 1% w/w when sprinkled on soft food for at least 30 minutes.

* * * * *